United States Patent
Tucker

(10) Patent No.: US 6,750,966 B2
(45) Date of Patent: Jun. 15, 2004

(54) REAL TIME MONITORING OF SMALL PARTICLE DISSOLUTION BY WAY OF LIGHT SCATTERING

(75) Inventor: Christopher J. Tucker, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/214,297

(22) Filed: Aug. 6, 2002

(65) Prior Publication Data

US 2004/0027569 A1 Feb. 12, 2004

(51) Int. Cl.$^7$ .............................................. G01N 21/00
(52) U.S. Cl. .......................... 356/338; 356/336; 424/61
(58) Field of Search ................................ 356/335–343, 356/36, 42; 250/574, 575; 424/61; 524/32, 413, 425; 60/648; 438/747

(56) References Cited

U.S. PATENT DOCUMENTS

| | | | |
|---|---|---|---|
| 3,710,113 A | * | 1/1973 | Padwer .................. 250/83.3 R |
| 5,485,728 A | * | 1/1996 | Dickinson .................... 60/648 |
| 5,681,877 A | * | 10/1997 | Hosotte-Filbert et al. ..... 524/32 |
| 5,710,069 A | * | 1/1998 | Farkas et al. .................. 438/7 |
| 5,958,385 A | * | 9/1999 | Tondeur et al. ............... 424/61 |
| 6,191,853 B1 | * | 2/2001 | Yamaguchi et al. ........ 356/336 |

OTHER PUBLICATIONS

Lipinski, C. A. et al., "Experimental and Computational Approaches to Estimate Solubility and Permeability in Drug Discovery and Development Settings," *Advanced Drug Delivery Reviews*, vol. 46, 2002, pp. 3–26.

* cited by examiner

*Primary Examiner*—Frank G. Font
*Assistant Examiner*—Sang H. Nguyen

(57) ABSTRACT

A method for determining the percent of a solid material dissolved into a liquid medium is disclosed. The method comprises the steps of combining the solid material and the liquid medium; determining the initial solid concentration (i); determining the dynamic solid concentration (d) using a light scattering technique; and calculating the percent dissolved material according to the formula: $[(i-d)/i] \times 100$. Methods for determining dissolution rate and particle size using turbidity measurements are also disclosed.

20 Claims, 4 Drawing Sheets

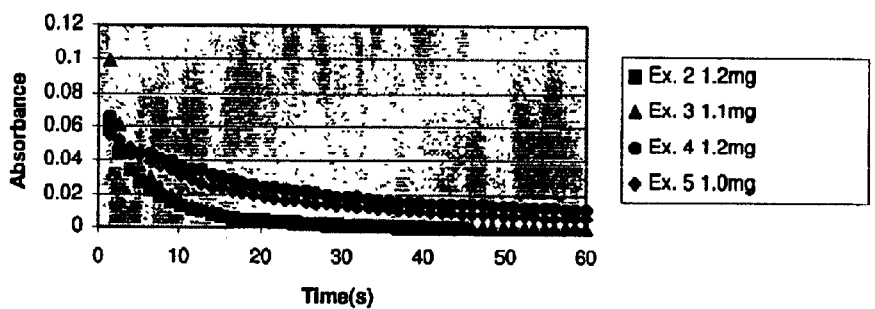
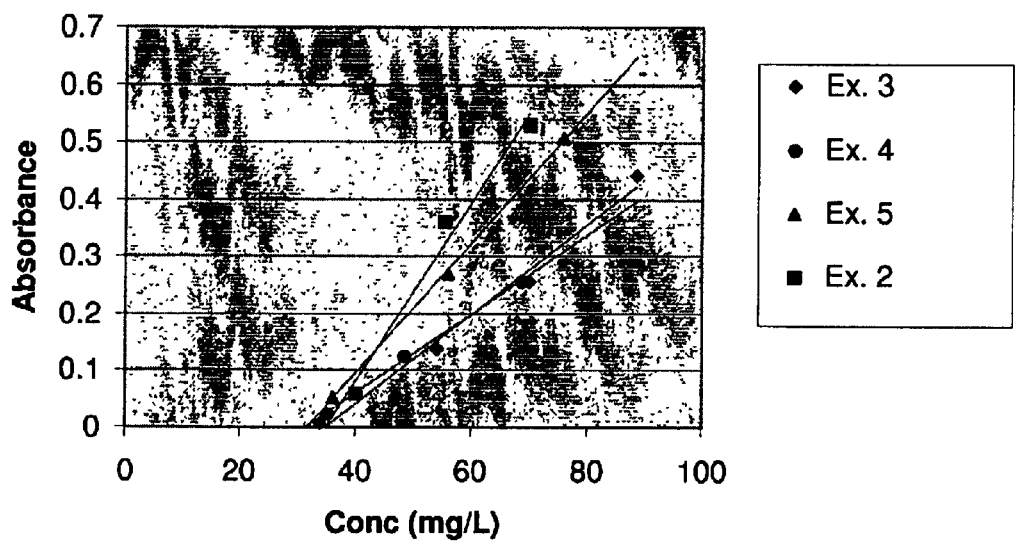

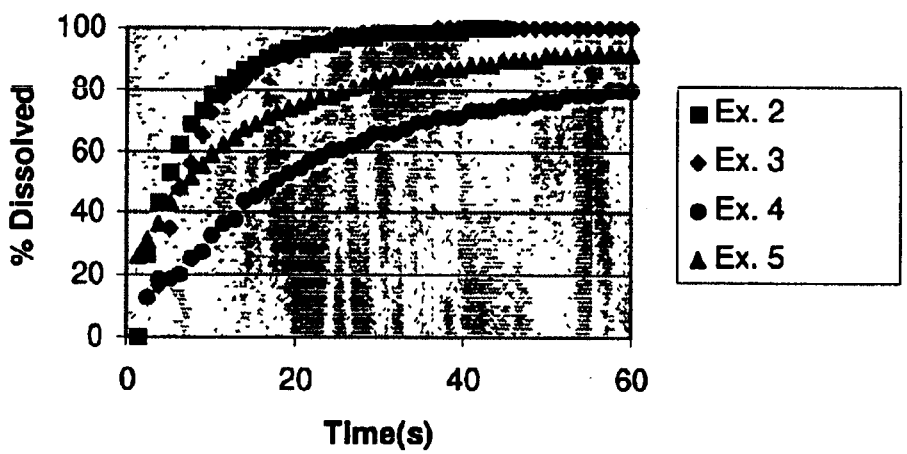
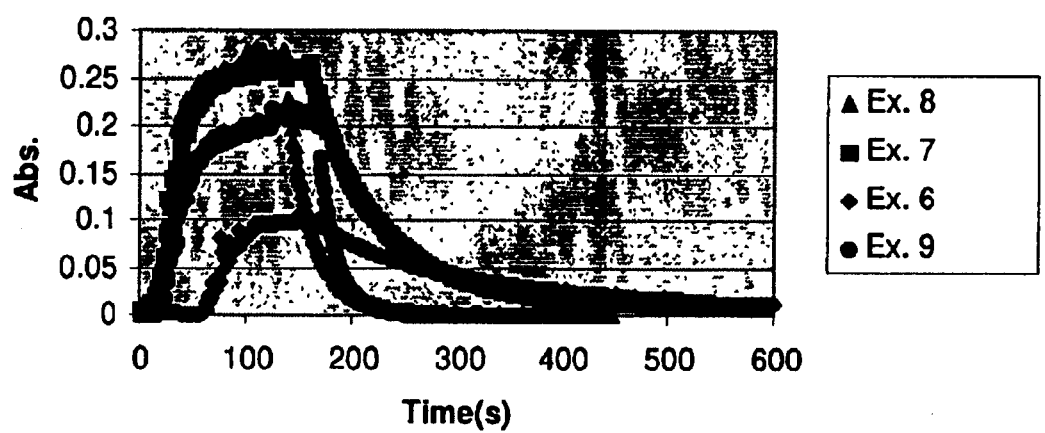

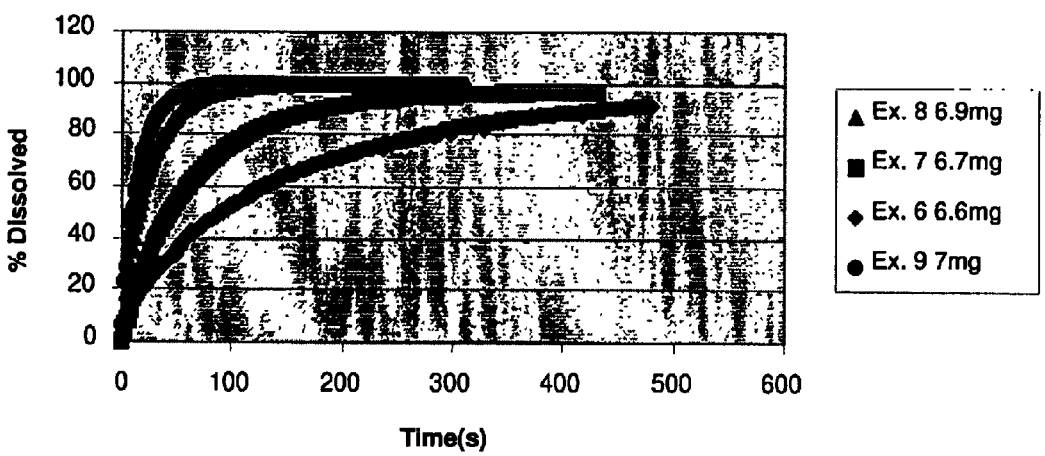
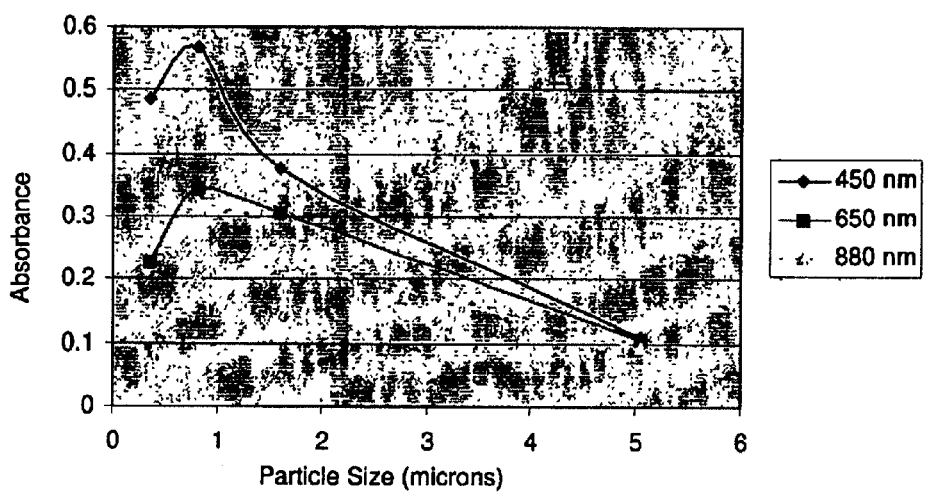

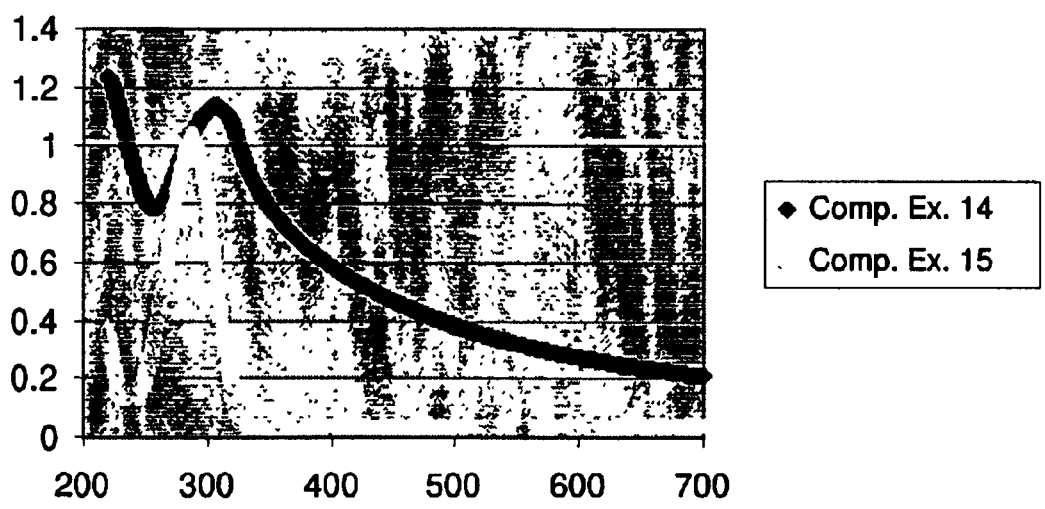

REAL TIME MONITORING OF SMALL PARTICLE DISSOLUTION BY WAY OF LIGHT SCATTERING

FIELD OF THE INVENTION

The present invention relates to a method for determining the dissolution rate of small particles and more particularly relates to determining the dissolution rate of small particles by way of light scattering methods.

DESCRIPTION OF PRIOR ART

High bioavailability and short dissolution times are desirable attributes of a pharmaceutical end product. Bioavailability is a term meaning the degree to which a pharmaceutical product, or drug, becomes available to the target tissue after being administered to the body. Poor bioavailability is a significant problem encountered in the development of pharmaceutical compositions, particularly those containing an active ingredient that is poorly soluble in water. Poorly water soluble drugs tend to be eliminated from the gastrointestinal tract before being absorbed into the circulation.

Dissolution time is one indication of bioavailability. Dissolution time is defined as the time it takes for a certain amount of material to dissolve in a liquid. Dissolution time is typically measured by first adding the drug substance to a dissolution media, then sampling that media at various times, filtering to remove undissolved materials, followed by HPLC analysis of the filtrate to determine the amount of dissolved drug. However, these methods measure static dissolution and are not suitable for measuring the dynamic, or real time dissolution of a material. HPLC methods are also relatively time consuming and inefficient. Moreover, HPLC methods provide very little discernment of enhancements in dissolution rates.

One method that can be used to measure dynamic dissolution is ultraviolet (UV) measurement. However, UV methods are only useful when the molecule being measured absorbs light in the UV region. In addition, UV methods are limited by the particle size of the molecule being measured. As the size of the particles being measured approaches the wavelength of the light source, scattering interferes, so measurement of absorption becomes impossible because the scattering of the wavelength of light in question interferes with the measurement. In addition, UV methods provide very little discernment of enhancements in dissolution rates for small particles.

An alternative method to measure dissolution is turbidity, which is typically a value indicating the quantity of particles suspended in a liquid. Turbidity gives a quantitative measurement of the change of intensity of light passing through the medium, caused by absorptive interactions resulting in energy transfer to the medium and by scattering from optical inhomogeneities in the medium. "Absorbance" is also a term that is used interchangeably with turbidity.

In "Experimental and computational approaches to estimate solubility and permeability in drug discovery and development settings, C. A. Lipinski et al., Advanced Drug Delivery Reviews 46 (2001), 3–26., turbidity has been used to predict the solubility of a drug. In Farinato and Rowell, Encyclopedia of Emulsion Technology, Vol. 1 pp. 444–451 (1983), turbidity is described as being useful for determining particle size for relatively large particles. However, these references refer only to "snapshot", static quantities of dissolved material and do not describe the use of turbidity to measure dynamic dissolution times. Moreover, these references do not describe measuring particle sizes for small particles in addition to measuring dissolution rates.

It would be an advantage to provide an alternative method for determining dissolution time which could be used to detect dynamic dissolution time, which could be used to detect the size of small particles, and which could be used quickly and efficiently. It would also be an advantage to provide a simple technique that can be used in a variety of environments and at a variety of scales, either large or small.

SUMMARY OF THE INVENTION

In one aspect, the present invention is a method for determining the percent of a solid material dissolved into a liquid medium comprising combining the solid material and the liquid medium; determining the initial solid concentration (i); determining the dynamic solid concentration (d) using a light scattering technique; and calculating the percent dissolved material according to the formula: $[(i-d)/i] \times 100$.

In a second aspect, the present invention is a method for determining the dissolution rate of a solid material dissolved into a liquid medium comprising combining the solid material and the liquid medium; determining the initial solid concentration (i); waiting for a period of time (T); determining the dynamic solid concentration (d) using a light scattering technique; and calculating the dissolution rate of the solid material according to the formula: $(i-d)/T$.

In a third aspect, the present invention is a method for determining the particle size of a drug substance dispersed in a liquid medium, wherein the concentration of the solid material in the liquid medium is known, comprising measuring the turbidity of the dispersion; and calculating the particle size of the drug substance from the turbidity measurement.

The present invention enables the determination of percent dissolved material on a dynamic basis. The present invention also enables a better scrutiny of changes in percent dissolved material than the methods used previously. The present invention also provides a simple method to measure dissolution at a variety of scales, including at a very large commercial scale or at a very small miniaturized scale.

BRIEF DESCRIPTION OF THE DRAWINGS

FIG. 1 is a graph depicting absorbance over time when using the present invention, more specifically described in Examples 1 through 5.

FIG. 2 is a calibration curve useful with the present invention, more specifically described in Examples 1 through 5.

FIG. 3 is a graph depicting percent dissolved material over time, more specifically described in Examples 1 through 5.

FIG. 4 is a graph depicting absorbance over time, more specifically described in Examples 6 through 9.

FIG. 5 is a graph depicting percent dissolved material over time, more specifically described in Examples 6 through 9.

FIG. 6 is a graph depicting absorbance versus particle size, more specifically described in Examples 10 through 13.

FIG. 7 is a graph depicting UV spectra, more specifically described in Comparative Examples 14 and 15.

DETAILED DESCRIPTION OF THE INVENTION

The present invention is directed to measurement of dissolution of a solid material into a liquid. Dissolution time is defined as the time it takes for a certain amount of solid material to dissolve in a liquid. The terms "solid" and "solid material" are used interchangeably herein and are defined to mean the active ingredient in the solid phase.

Preferably, the solid material comprises a drug substance. Advantageously, the drug substance is poorly soluble in water. Suitable drug substances can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, anti-muscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiacinotropic agents, contrast media, corticosterioids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasidilators and xanthines. Preferred drug substances include those intended for oral administration. A description of these classes of drugs and a listing of species within each class can be found in Martindale, The Extra Pharmacopoeia, Twenty-ninth Edition, The Pharmaceutical Press, London, 1989.

The present invention is particularly advantageous when the solid material has a small average particle size. Desirably, the solid material has an average particle size of less than about 50 microns, more preferably less than about 20 microns and even more preferably less than about 10 microns. Desirably, the solid material has an average particle size of at least about 0.05 microns, more preferably at least about 0.1 microns, and even more preferably at least about 0.2 microns. Outside of these ranges, problems may be encountered due to reduced scattering efficiency. Also, when particles are too large, one might encounter difficulties in maintaining a homogeneous dispersion of particles, due to settling or creaming.

The solid material is combined with a liquid medium. Any liquid medium can be used, so long as the liquid medium is transparent in visible light and has a sufficiently different refractive index from the solid material such that the solid scatters light. The liquid medium should be chosen such that the equilibrium solubility of the solid material in the liquid medium is between 5 and 500 mg/L of the active ingredient in the solid material, more preferable between 10 and 200 mg/L, even more preferably between 20 and 100 mg/L. The term "equilibrium solubility" is defined herein to mean that the maximum amount of solid material that can be completely dissolved within 120 minutes in the liquid medium using this technique. Advantageously, an equilibrium solubility within this range provides for good sensitivity and a linear relationship between concentration and turbidity, allowing for a simplified correlation between concentration and turbidity.

Examples of suitable liquid media include water, water/alcohol blends, water/surfactant solutions, and water/electrolyte solutions. The liquid medium could also be a solvent such as an alcohol. In a preferred embodiment, the liquid medium is water.

As the solid material is combined with the liquid medium, the solid will first disperse into the liquid before it begins to dissolve in the liquid. As the liquid and solid are combined, some level of agitation may be necessary to maintain a homogenous dispersion. For smaller particles, for example, for particles less than 1 micron, agitation is less critical, but for larger particles, especially those greater than 5 microns, agitation is more critical to maintain a homogeneous dispersion As long as the solubility of the solid material combined with the liquid medium falls within the range of the equilibrium solubility described above, the temperature at which the solid material and the liquid medium are combined is not critical. Any temperature between the freezing point and the boiling point of the liquid medium is appropriate. The pressure at which the solid and liquid are combined is not critical, as long as the equilibrium solubility falls within the range described above. Preferably, the solid and liquid are combined at ambient conditions.

Before the solid material and the liquid medium are combined, or as soon as possible thereafter, the initial solid concentration, referred to herein as "i", is determined. Determination of i can be performed by calculating the theoretical concentration based upon the weight of the solid material and the volume of the liquid medium. Alternatively, i can be measured using instrumentation, such as light scattering instrumentation, after combining the solid material and the liquid medium. In such a case, one would need to develop a calibration curve showing turbidity versus a known concentration for the particular solid material used. One would then calculate i from the calibration curve based upon a measurement of turbidity.

Preferably, i is such that the initial solid concentration is from about 5 to about 95% of the equilibrium solubility for the particular solid material and liquid medium used. More preferably, i is from about 10 to about 90% of the equilibrium solubility, and even more preferably, i is from about 40 to about 80% of the equilibrium solubility. If i is too far below the equilibrium solubility, then the dissolution occurs quickly, making it difficult to accurately measure rates of dissolution using this technique. If i is above the equilibrium solubility, then complete dissolution does not occur, making it difficult to measure dissolution rates using the technique of the present invention.

After the solid is dispersed in the liquid and i is determined, the solid will begin to dissolve in the liquid. As the solid dissolves, the dynamic solid concentration, referred to herein as "d", can be determined. The term "dynamic" is defined herein to mean that the solid in liquid is not at equilibrium. As a result, the measurement of d occurs as the solid concentration is changing, in other words, as the solid is dissolving in the liquid. There is not a substantial delay between the change in solid concentration and the measurement of solid concentration d.

To measure d, a light scattering technique is used. Such techniques employ light in the visible light region. The use of visible light is advantageous over the use of ultraviolet light because the use of a longer wavelength light avoids absorption of light by dissolved solid material. Examples of light scattering techniques which may be used include low angle laser light scattering, light transmittance, colorimetry, and turbidity. In a preferred embodiment, turbidity is used to measure d.

The dynamic solid concentration, d, can be measured at a single point in time, or, in a preferred embodiment, d is measured at multiple points in time as the solid is dissolving in the liquid medium. If d is measured at multiple points in time, a curve results. A comparison of curves developed for different solid/liquid systems allows for a determination of slight differences in dissolution rates among the different systems.

The determination of i and d are then used to determine the percent dissolved material according to the formula:

% dissolved solid material=$[(i-d)/i] \times 100$.

In a preferred embodiment, one or more solutes is also combined with the solid and the liquid. In fact, in some cases, the solid will not noticeably dissolve until after an solute has been added to the liquid medium. The solute can be present in the liquid before the solid and liquid are combined, or the solute can be added to the solid-liquid dispersion after the solid and liquid are combined. The solute can be added to adjust the equilibrium solubility, and/or to ensure that the properties of the liquid medium, such as pH, remain constant. Examples of solutes suitable for use with the present invention include stabilizers, surfactants, pharmaceutically-acceptable excipients, electrolytes, acids or bases, buffers, artificial G.I. tract and stomach fluids, polymers, absorption enhancers, solubility enhancing agents, dissolution rate enhancing agents, bioadhesive agents, controlled release agents and the like.

The present invention is also useful for determining the rate of dissolution of dissolved material. In such an embodiment, the technique described above is followed, and the time T it takes for the solid concentration to change from i to d is also measured. The dissolution rate can then be determined according to the formula:

dissolution rate=$(i-d)/T$.

In one embodiment of the present invention, the mean particle size for solid particles dispersed in a liquid medium can be determined. In order to determine particle size, the concentration of the solid material in the liquid medium must be known. The turbidity of the dispersion is first measured as with the techniques described above. The particle size of the drug is then determined from the turbidity measurement. Optimally, a calibration curve is first created using various dispersions containing particles of a known size. The calibration curve will plot turbidity against particle size.

EXAMPLES

Comparative Example 1 and Examples 2 through 5

Measurement of Percent Dissolved Material for Wet Milled Particles of Naproxen.

For each of Comparative Example 1 and Examples 2 through 5, particles were prepared using a wet milling technique. Various sized particles of the drug were prepared with identical excipient levels using a wet milling technique. 1.35 grams of Naproxen, 13.5 g of a solution of 29,000 molecular weight poly vinyl pyrolidinone, and 100 g of 1 mm diameter ZrO milling beads were combined in a 2 oz. wide-mouth jar. The jar was then placed on a rotating ball mill and taken off at the time indicated in Table A below. The sample was then filtered to remove the milling beads and the filtrate freeze dried to give a powder. Particle sizes were determined by redispersing the particles to 1% solids in water and performing low angle laser light scattering using a Coulter LS230 Particle size analyzer. The results are indicated in Table A below.

TABLE A

| Example | Milling Time | Mean Particle Size (microns) |
|---------|--------------|------------------------------|
| 1 (Comp.) | none | 54 |
| 2 | 7 hrs. | 0.656 |
| 3 | 48 hrs. | 0.266 |
| 4 | 1 hr. | 4.757 |
| 5 | 3 hrs. | 1.919 |

For each of Examples 1 through 5, dissolution evaluation was performed by weighing 1.0 to 1.5 mg of the sample to be tested into a glass vial. To this vial was then added sufficient water to prepare a 1 wt % suspension of the sample material. The suspension was agitated to ensure redispersion to particles and the resulting suspension added to 150 ml of an aqueous media (0.1% HCl in water). The acidic solution was used to ensure that no solubilization due to neutralization of the acidic (pKa=4.2) Naproxen occurred. The turbidity at 450 nm was then monitored as a function of time using a Brinkman 910 PC calorimeter to give the plots shown in FIG. 1. The term "absorbance" is used herein interchangeably with turbidity, such that the absorbance number equals the turbidity for the particular sample tested.

To convert the plots depicted in FIG. 1 to percent dissolved material, a calibration curve was first determined for the samples of Comparative Example 1 and Examples 2 through 5. This was done by first placing 150 ml of dissolution media (0.1% HCl) in a beaker and then adding 1-2 mg aliquots of the sample being evaluated. For each addition the absorbance was monitored until it remained constant at which time another 1-2 mg of the sample was added and the process repeated. This allows for the generation of a plot of absorbance vs. particle concentration such as those shown in FIG. 2.

The calibration curves for Examples 2 through 5 look nearly identical. This indicates that the sensitivity of the technique at these particle sizes is nearly identical. At a particle size of 50 microns and greater (Comparative Example 1), the sensitivity is low enough that the technique is difficult to use at this dosage level. Also, at all particle sizes one sees an intercept at about the same value. This is the equilibrium solubility for a 1/1 blend of Naproxen and Polyvinyl pyrolidinone in 0.1% HCl. Using the above calibration curve one can convert the absorbance numbers to percent dissolved material to get the plots depicted in FIG. 3.

Examples 6 through 9

Measurement of Percent Dissolved Material for Wet Milled Particles of Danazol.

Another embodiment for the method of the present invention is to dose a sample into a solution at levels above it's equilibrium solubility in that media, agitate the suspension to redisperse to particles, then add a solubulizing ingredient to increase the samples equilibrium solubility to a level above the concentration of the suspension and monitor the decrease in turbidity vs. time. For Examples 6 through 9, the same milling technique as described above for example 1 through 5 was used. Danazol powders were prepared via wet milling using Poloxamer F127 (1 to 1 ratio to Danazol by weight). The particle sizes for the resulting powders when redispersed in water and measured using a Coulter LS230 particle size analyzer are shown in Table B.

TABLE B

| Example | Milling Time | Mean Particle Size (microns) |
|---|---|---|
| 6 | none | 5.05 |
| 7 | 1 hr. | 1.599 |
| 8 | 3 hrs. | 0.817 |
| 9 | 39 hrs. | 0.356 |

The dissolution profiles were obtained by adding 6–7 mg of each of the powders to a 200 ml beaker containing 150 ml of deionized water, a 1" octagonal stir bar and a turbidity probe with a 650 nm light filter connected to a Beckman 910 PC Colorimeter. For the first 120 seconds the stir bar was set at a speed to give minimal agitation. This allows one to characterize the redispersion of the powder. At 120 seconds the stir rate was turned to its maximum. At 150 seconds the stir rate was turned back down to a speed just below that at which a vortex forms. At approximately 165 seconds 2.25 grams of a 20% solution of sodium dodecyl sulfate was added to the suspension. The addition of this amount sodium dodecyl sulfate increases the equilibrium solubility of Danazol from about 1 mg/l to about 45 mg/l. Using this procedure the turbidity curve shown in FIG. 4 was obtained. These examples demonstrate the utility of using light scattering techniques to characterize dissolution rates for small particles in liquid media.

The absorbance value just prior to the addition of the sodium dodecyl sulfate can be taken as the absorbance at 0% dissolved allowing one to calculate the percent dissolved from the difference between the turbidity measured at any given time and this reference value. Doing this with the plots above and resetting time zero to the time at which the sodium dodecyl sulfate solution was added gives the plot shown in FIG. 5.

Example 10 through 13

Determination of Particle Size

Using one embodiment of the present invention, turbidity, also referred to herein as absorbance, can be used to determine particle size from the initial absorbance for a known material with a monomodal particle size distribution. For each of the samples used in Examples 6, 7, 8 and 9, absorbance is plotted against the known particle size at various wavelengths and a constant concentration (30 mg/L), resulting in the plots shown in FIG. 6.

As shown in FIG. 6, the maximum scattering (absorbance) is seen for particles that have a mean diameter approximately twice the wavelength of the incident light. For particles larger than this value the absorbance at a given particle concentration decreases with increasing particle size. If one knows the concentration of an unknown one can use a graph such as shown in FIG. 6 to calculate a particle size. Note that in general one will obtain two possible solutions for the particle size. To distinguish between the two one can determine the absorbance at a different wavelength of incident light and see which particle size fits the data best. For instance if one obtains an absorbance of 0.300 for an Danazol dispersion at a drug concentration of 30 mg/liter using a 650 nm light source. From the plots in FIG. 6 one sees that two particle sizes—0.6 and 2.25 microns would be expected to give this absorbance. If one then changes the wavelength of the light source to 450 nm and measures the absorbance again one would see an absorbance of ~0.54 if the unknown has a particle size of 0.6 microns and ~0.37 if the unknown has a particle size of 2.25 microns.

Comparative Examples 14 and 15

Measurement of UV-vis Spectra for Samples of Danazol

The Ultraviolet spectra for these examples are shown in FIG. 7 and were obtained using a Shimadzu model UV-3101PC UV-Vis-NIR Scanning Spectrophotometer. In both Comparative Examples 14 and 15, the sample prepared according to Example 9 (average particle size of 0.356 microns) was used. In Comparative Example 14, the sample was dispersed as a solid material. In Comparative Example 15, sufficient amount of a solubilizing agent (sodium dodecyl sulfate) is added to obtain a concentration of 0.5 weight percent. From the results shown in FIG. 7, if one was to use the standard UV technique for determining dissolved drug concentration (UV absorption at max absorption) one could not distinguish between dissolved drug and drug suspended as a solid.

What is claimed is:

1. A method for determining the percent of a solid material dissolved into a liquid medium comprising:
    a. combining the solid material and the liquid medium, wherein the solid material has an average particle size of from about 0.05 microns to about 50 microns, and wherein the solid material has an equilibrium solubility in the liquid medium of between 5 and 500 mg/L;
    b. determining an initial solid concentration (i) of the solid material in the liquid medium;
    c. determining a dynamic solid concentration (d) using a light scattering technique; and
    d. calculating the percent dissolved material according to the formula:

$$[(i-d)/i] \times 100.$$

2. The method according to claim 1 wherein step b is performed using a weight calculation, a light scattering technique, or a combination thereof.

3. The method according to claim 2 wherein the light scattering technique is low angle laser light scattering, light transmittance, colorimetry, or turbidity.

4. The method according to claim 1 wherein the solid material comprises a drug substance.

5. The method according to claim 1 wherein the solid material has an average particle size of from about 0.2 microns to about 20 microns.

6. The method according to claim 1 wherein the quantity of solid material used in step a is equal to or less than about 0.2 mg when the amount of liquid is about 10.0 mL.

7. The method according to claim 1 wherein the liquid medium comprises a liquid that is transparent in visible light.

8. The method according to claim 7 wherein the liquid medium further comprises a solute.

9. The method according to claim 8 wherein the solute is one or more stabilizers, surfactants, pharmaceutically-acceptable excipients, electrolytes, acids or bases, buffers, artificial G.I. tract and stomach fluids, polymers, absorption enhancers, solubility enhancing agents, dissolution rate enhancing agents, bioadhesive agents, controlled release agents or combinations thereof.

10. A method for determining the dissolution rate of a solid material dissolved into a liquid medium comprising:
    a. combining the solid material and the liquid medium, wherein the solid material has an average particle size of from about 0.05 microns to about 50 microns, and wherein the solid material has an equilibrium solubility in the liquid medium of between 5 and 500 m/L;
b. determining an initial solid concentration (i);
c. waiting for a period of time (T);
d. determining a dynamic solid concentration (d) using a light scattering technique; and
e. calculating the dissolution rate of the solid material according to the formula:

(i−d)/T.

11. The method according to claim 10 wherein step b is performed using a weight calculation, a light scattering technique, or a combination thereof.

12. The method according to claim 11 wherein the light scattering technique low angle laser light scattering, light transmittance, colorimetry, or turbidity.

13. The method according to claim 10 wherein the solid material comprises a drug substance.

14. The method according to claim 10 wherein the solid material has an average particle size of from about 0.2 microns to about 20 microns.

15. The method according to claim 10 wherein the quantity of solid material used in step a is equal to or less than about 0.2 mg when the amount of liquid is about 10.0 mL.

16. The method according to claim 10 wherein the liquid medium comprises a liquid that is transparent in visible light.

17. The method according to claim 16 wherein the liquid medium further comprises a solute.

18. The method according to claim 17 wherein the solute is one or more stabilizers, surfactants, pharmaceutically-acceptable excipients, electrolytes, acids or bases, buffers, artificial G.I. tract and stomach fluids, polymers, absorption enhancers, solubility enhancing agents, dissolution rate enhancing agents, bioadhesive agents, controlled release agents or combinations thereof.

19. A method for determining particle size of a drug substance dispersed in a liquid medium, wherein the particle size is expected to be in the range of from about 0.05 microns to about 50 microns and wherein the drug substance has an equilibrium solubility in the liquid medium of between 5 and 500 mg/L, comprising:

measuring turbidity of the dispersion; and
calculating the particle size of the drug substance from the turbidity measurement.

20. The method according to claim 19 wherein the particle size is calculated using a calibration curve depicting turbidity versus particle size.

* * * * *